(12) United States Patent
De Samber et al.

(10) Patent No.: US 11,246,197 B2
(45) Date of Patent: Feb. 8, 2022

(54) LIGHT SOURCE AND METHOD FOR AUGMENTING COLOR PERCEPTION FOR COLOR DEFICIENT PERSONS

(71) Applicant: SIGNIFY HOLDING B.V., Eindhoven (NL)

(72) Inventors: Marc Andre De Samber, Lommel (BE); Norbertus Antonius Maria Sweegers, Lierop (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 308 days.

(21) Appl. No.: 16/496,990

(22) PCT Filed: Mar. 23, 2018

(86) PCT No.: PCT/EP2018/057485
§ 371 (c)(1),
(2) Date: Sep. 24, 2019

(87) PCT Pub. No.: WO2018/177944
PCT Pub. Date: Oct. 4, 2018

(65) Prior Publication Data
US 2021/0329754 A1 Oct. 21, 2021

(30) Foreign Application Priority Data
Mar. 28, 2017 (EP) ..................... 17163356

(51) Int. Cl.
*H05B 45/20* (2020.01)
*F21V 9/40* (2018.01)
(Continued)

(52) U.S. Cl.
CPC ............... *H05B 45/20* (2020.01); *F21V 9/40* (2018.02); *F21W 2131/405* (2013.01); *F21Y 2115/10* (2016.08)

(58) Field of Classification Search
CPC . H05B 45/20; F21V 9/40; F21V 23/04; F21K 9/64; F21K 9/65; F21W 2131/405
See application file for complete search history.

(56) References Cited

U.S. PATENT DOCUMENTS 6,153,971 A * 11/2000 Shimizu ................. C09K 11/76
252/301.4 P
6,414,426 B1 7/2002 Akashi et al.
(Continued)

FOREIGN PATENT DOCUMENTS

| CN | 101657876 A | 2/2010 |
|---|---|---|
| CN | 102934523 A | 2/2013 |

(Continued)

OTHER PUBLICATIONS

"How is white light made with LEDs", NLPIP, vol. 7, Issue 3, p. 1-2.

*Primary Examiner* — Abdullah A Riyami
*Assistant Examiner* — Syed M Kaiser
(74) *Attorney, Agent, or Firm* — Daniel J. Piotrowski

(57) ABSTRACT

The invention provides a lighting system (1) comprising a lighting device (100) configured to provide lighting device light (101) with a variable spectral distribution (SD), wherein the lighting system (1) comprises a control system configured to control the spectral distribution (SD) of the lighting device light (101), wherein the lighting device (1) comprises at least two lighting modes (M1,M2), wherein: 5 (i) in a first lighting mode (M1) the lighting device (1) is configured to provide white light (101) with a first spectral distribution (SD1) in the visible with a first spectral intensity P1, the first spectral distribution (SD1) having a spectral intensity gap (G) configured in the spectral range of 430-600 nm, the spectral intensity gap (G) having a spectral gap width (GW1) of at least 20 nm and a maximum spectral gap intensity PG1 of lighting device light (101) within the (Continued)

spectral intensity gap (G) of PG1/P1≤k, wherein k is a predefined intensity ratio value, and (ii) in a second lighting mode (M2) the lighting device (1) is configured to provide white light (101) with a second spectral distribution (SD2) with a second spectral intensity P2, with a relatively enhanced intensity P2* of the lighting device light (101) in the same spectral range of the spectral intensity gap (G) of the first lighting mode, wherein P2*/P2>k.

15 Claims, 5 Drawing Sheets

(51) Int. Cl.
    *F21W 131/405*     (2006.01)
    *F21Y 115/10*     (2016.01)

(56) References Cited

U.S. PATENT DOCUMENTS

| | | | |
|---|---|---|---|
| 2005/0104040 A1 | 5/2005 | Mendelsohn | |
| 2008/0252197 A1 | 10/2008 | Li et al. | |
| 2013/0088154 A1 | 4/2013 | Van Hoof et al. | |
| 2015/0162505 A1* | 6/2015 | Jones | F21K 9/64 362/293 |
| 2016/0025304 A1 | 1/2016 | Wagemans et al. | |
| 2016/0169459 A1 | 6/2016 | Van Bommel et al. | |
| 2016/0223146 A1 | 8/2016 | Vick et al. | |
| 2016/0243379 A1* | 8/2016 | Hommes | F21K 9/64 |
| 2016/0323959 A1 | 11/2016 | Rooymans | |
| 2017/0045201 A1* | 2/2017 | Jones | F21V 7/30 |
| 2017/0176336 A1* | 6/2017 | Dimitriadis | A61B 3/14 |

FOREIGN PATENT DOCUMENTS

| | | |
|---|---|---|
| CN | 103688145 A | 3/2014 |
| CN | 104854399 A | 8/2015 |
| CN | 105265025 A | 1/2016 |
| JP | 2008-047465 A | 2/2008 |
| JP | 2009158823 A | 7/2009 |
| JP | 2012-028270 A | 2/2012 |
| JP | 2014-216295 A | 11/2014 |
| KR | 20170001408 A | 1/2017 |
| WO | 2015184299 A1 | 12/2015 |
| WO | 2016146688 A1 | 9/2016 |
| WO | 2016188755 A1 | 12/2016 |
| WO | 2017036789 A1 | 3/2017 |

* cited by examiner

LIGHT SOURCE AND METHOD FOR AUGMENTING COLOR PERCEPTION FOR COLOR DEFICIENT PERSONS

CROSS-REFERENCE TO PRIOR APPLICATIONS

This application is the U.S. National Phase application under 35 U.S.C. § 371 of International Application No. PCT/EP2018/057485, filed on Mar. 23, 2018, which claims the benefit of European Patent Application No. 17163356.3, filed on Mar. 28, 2017. These applications are hereby incorporated by reference herein.

FIELD OF THE INVENTION

The invention relates to a lighting system and also to a retail lighting system comprising such lighting system.

BACKGROUND OF THE INVENTION

Systems and methods for expanding human perception are known in the art. WO2015/184299, for instance, describes media and devices that exploit the possibility of encoding multiple channels of spatially structured information into single images, by exploiting temporal modulation of color and brightness, are proposed. Applications include relief of color blindness, producing images enriched with normally "invisible" information from infrared, ultraviolet, and polarization, and effectively adding new perceptible colors within the visible spectrum. Amongst others, this document describes a system comprising: at least one sensor configured to detect at least one characteristic of an object that is not perceptible to an unaided human observer, the at least one characteristic being described by at least one measurement; at least one processor in data communication with the sensor; one or more components executable by the at least one processor and collectively configured to:

receive, from the at least one sensor, data descriptive of the object and the at least one measurement; and generate an enhanced image of the object including an attribute representative of the measurement that is perceptible by the human observer, that systematically varies over time, and that is localized and faithful to a non-enhanced image of the object.

SUMMARY OF THE INVENTION

People with 'faulty' trichromatic vision will be color blind to some extent and are known as anomalous trichromats. In people with this condition all of their three cone types are used to perceive light colors but one type of cone perceives light slightly out of alignment, so that there are three different types of effect produced depending upon which cone type is 'faulty'. The different anomalous conditions are protanomaly, which is a reduced sensitivity to red light, deuteranomaly which is a reduced sensitivity to green light and is the most common form of color blindness and tritanomaly which is a reduced sensitivity to blue light and is extremely rare.

Color vision deficiency (aka color blindness) affects approximately 1 in 12 men (8%) and 1 in 200 women in the world. There are a number of causes and types of color blindness. It is known from human physiology that some types of color deficiency result from a congenital lower sensitivity of retinal receptors (cones), leading to miss-interpretation or the inability to differentiate between certain colors (for example between specific types of green and red). It is the purpose of this invention to come with a solution for such type of color deficiency, in which persons the color receptors are present and active but show the mentioned lowered sensitivity.

Color deficiency is not a disease but rather a reduced functionality in human, but does lead to a number of more or less important symptoms. For example, not being able to recognize colors in traffic lights can lead to dangerous situations.

A possibility to enhance color perception is to use goggles that filter out part of the light. The use of goggles, however, has two major disadvantages: it provides only a fixed (not tunable) color filter function (while color deficiency is very variable person-to-person), it is requiring an action ('wearing goggles') from the user and draws possibly undesired attention ('goggles are colored'). It would be highly preferred to provide a solution with a versatile, tunable and non-obtrusive light source that takes over the function of the goggles and also provides a solution to the mentioned two issues.

Hence, it is an aspect of the invention to provide an alternative solution, which preferably further at least partly obviates one or more of above-described drawbacks. The present invention may have as object to overcome or ameliorate at least one of the disadvantages of the prior art, or to provide a useful alternative.

In the present invention, we suggest amongst others a solution based on a retail (shop) light system that will provide help for color deficient people in shopping, easing their choice in e.g. clothing by giving them a more correct perception of color and also leading to the selection of 'generally' accepted/expected color setting of his/her clothing (not leading to 'strange' choices). Also, shopping for e.g. fruits could be made easier by providing the color deficient person the chance to distinguish between ripe and non-ripe fruits (green versus reddish).

Amongst others, it is suggested herein to provide a light source (or a group of light sources) in which the emission color spectrum is highly tunable, mainly in the wavelength segments where there is a (varying) overlap in the color bands that are causing the problem (e.g. green-red, which is the majority of color deficient cases, but also blue-yellow). Such light spectrum may be created by the use of narrow band light sources or narrow band phosphors, which provide narrow emission bands in the total spectrum and are addressable (can be turned on/off and steered in intensity). In specific embodiments, an environment, e.g. the inside of a shop, a fitting room in a clothing shop that is suitable for the envisioned function can be chosen to provide the light, especially in dependence of a (sensor) signal. Such an environment that offers a light setting (sufficiently dimmed light of other light sources) such that the solution may work. Further, a user interface for the user/customer may be provided, allowing him/her to change the illuminating light spectrum such that colors become more distinguishable. Such interface being manual (e.g. a simple rotating nob), a touchpad with icons (showing e.g. color deficiency type), or a combination of these (e.g. with coarse and fine tuning) Hence, interfacing and steering of the system might also optionally be provided by an unobtrusive App function in e.g. a personal smartphone, which might then also contain the personal and specific color settings that are optimal for the person in case.

Hence, in a first aspect the invention provides a lighting system ("system") comprising a lighting device configured to provide lighting device light ("light") with a variable spectral distribution wherein the lighting system comprises a control system ("controller") configured to control the spectral distribution of the lighting device light, wherein the lighting device comprises at least two lighting modes wherein:

(i) in a first lighting mode the lighting device is configured to provide visible light, especially white light, with a first spectral distribution in the visible with a first spectral intensity P1, the first spectral distribution having a spectral intensity gap ("gap" or "spectral gap") configured in a first spectral range of 440-490 nm or a second spectral range of 510-580 nm, the spectral intensity gap having a spectral gap width (GW1) of at least 20 nm and a maximum spectral gap intensity PG1 of lighting device light within the (spectral range of the) spectral intensity gap of $PG1/P1 \leq 0.2$, and (ii) in a second lighting mode the lighting device is configured to provide white light with a second spectral distribution with a second spectral intensity P2, with a relatively enhanced intensity P2* of the lighting device light in the same spectral range of the spectral intensity gap of the first lighting mode, wherein $P2^*/P2 > 0.2$, and the lighting system further comprising a plurality of light sources that are configured to provide light source light with wavelengths solely within the spectral intensity gap, wherein the control system is configured to control the plurality of light sources in dependence of one or more of an input signal of a user interface and a sensor.

With such system, it is possible to provide white light that is especially adapted for a color blind person, such that the color blind person may better perceive colors. Further with such system it is possible to change the spectral distribution of the light with no or relatively low impact on the perception of the light of the system. Hence, relatively discreetly the light may be changed from the second spectral distribution to the first spectral distribution and back. Further, with such system color blind people do not need to use goggles, which may also be appreciated by many color-blind people.

The term white light herein, is known to the person skilled in the art. It especially relates to light having a correlated color temperature (CCT) between about 2000 and 20000 K, especially 2700-20000 K, for general lighting especially in the range of about 2700 K and 6500 K, and for backlighting purposes especially in the range of about 7000 K and 20000 K, and especially within about 15 SDCM (standard deviation of color matching) from the BBL (black body locus), especially within about 10 SDCM from the BBL, even more especially within about 5 SDCM from the BBL.

As indicated above, the lighting system comprises a lighting device configured to provide lighting device light with a variable spectral distribution. The term "lighting device" may also relate to a plurality of (different) lighting devices. Hence, the lighting system may comprise one or more lighting devices as defined herein, and optionally also one or more other lighting devices (which may e.g. not be spectrally tunable).

During use, the lighting device may produce light with a variable spectral distribution. For instance, the lighting device may be configured to provide light with one or more different colors, one or more different color points, one or more different color temperatures. The spectral properties of the lighting device light are controlled by the control system.

Hence, the lighting system comprises a control system configured to control the spectral distribution of the lighting device light. As indicated above, the lighting system may comprise a plurality of light sources with two or more subsets of each at least a single lighting device, wherein the subsets may be individually controllable by the control system.

The term "controlling" and similar terms especially refer at least to determining the behavior or supervising the running of an element, such as the lighting device light. Hence, herein "controlling" and similar terms may e.g. refer to imposing behavior to the element (determining the behavior or supervising the running of an element), etc., such as e.g. measuring, displaying, actuating, opening, shifting, changing temperature, etc. Beyond that, the term "controlling" and similar terms may additionally include monitoring. Hence, the term "controlling" and similar terms may include imposing behavior on an element and also imposing behavior on an element and monitoring the element.

Whatever tunability the lighting device(s) may have, the lighting device in embodiments alone or in other embodiments in combination with one or more other lighting devices comprises at least two lighting modes wherein white light is provided, but with different spectral properties.

In a first mode, which may especially be useful for color blind people, a specific band in the visible spectrum is not available or only with a low intensity. For instance, it appears that a deficit of yellow light may assist color recognition by red-green color blind people. In a second lighting mode, which may e.g. a default mode, this gap may have a higher intensity. In this way, different types of white light may be provided while e.g. one or more spectral properties selected from the group of color point, color temperature, CRI, R8, etc. etc., may essentially be the same. The first mode may be chosen by a color blind person to assist in observing items, like a painting, (security) information, a product (for sale), clothes, a wearable, etc. etc. The light in the first mode is especially white light, such as having a color point especially within about 15 SDCM (standard deviation of color matching) from the BBL (black body locus). Optionally, to obtain white light in the first mode, an additional light source may be used. In this way, an modified first mode may (also) be obtained. Especially, the user can choose this the first spectral distribution to fit best with the color deficiency.

Therefore, the lighting device comprises at least two lighting modes wherein: (i) in a first lighting mode ("first mode") the lighting device is configured to provide visible light, especially white light, with a first spectral distribution in the visible with a first spectral intensity P1, the first spectral distribution having a spectral intensity gap with a low intensity, or even an essentially zero intensity, and (ii) in a second lighting mode ("second lighting mode") the lighting device is configured to provide white light with a relatively enhanced intensity of the lighting device light in the same spectral range of the spectral intensity gap of the first lighting mode. Hence, the invention allows an on and off switching of a spectral region for facilitating enhanced vision of color blind people. Not only switching may be allowed, the shape and intensity of more parts of the visible spectrum may change from one mode to the other, for instance to keep the spectral properties (of the light in the two modes), such as indicated above, essentially the same. The intensities, especially the (first) spectral intensity and the intensity within the spectral intensity gap are especially evaluated in photon counts (i.e. (total) number of photons (in the visible), unless indicated otherwise or clear from the context.

In embodiments, the first mode the lighting device provides colored light and optionally one or more additional light sources provide also colored light (in the spectral intensity gap), to provide together white light (together especially providing white light with a better color perception for color blind people).

In embodiments, the first mode the lighting device provides white light and optionally one or more additional light sources provide also colored light (in the spectral intensity gap), to provide together white light (especially with a better color perception for color blind people).

In a first lighting mode the lighting device is configured to provide visible light, especially white light, with a first spectral distribution in the visible with a first spectral intensity P1, the first spectral distribution (thus) having a spectral intensity gap especially configured in the spectral range of 430-600 nm, the spectral intensity gap having a spectral gap width of at least 20 nm and a maximum spectral gap intensity PG1 of lighting device light within the spectral intensity gap of PG1/P1≤k, wherein k is a predefined intensity ratio value. The value of k is equal to or larger than 0.

Hence, a part k or a part*100% k is the relative intensity in the spectral intensity gap, and 1-k, or 100-100%*k is the intensity in the remainder of the spectrum. As indicated above, the remainder of the spectrum provides essentially white light, as the intensity in the gap is relatively low. If a better fit with white light is envisioned and/or special effects or accents may be desired, then one can also further change the spectral distribution in other parts of the spectral distribution, for instance to even better approach white. For instance, k≤0.2, especially k≤0.1, such as k≤0.0.05. In specific embodiments, k may be predefined in the system. In yet further embodiments, a maximum k value may be predefined in the system. In embodiments, k may be influenced (via a user interface) by a user (in embodiments up to a predefined maximum k value. In yet another embodiments, settings might be implemented as learnt from history of user selected settings.

The spectral gap is especially configured in the range of 430-600 nm, such as in the yellow. The gap width is especially at least 20 nm, even more especially the spectral gap width (GW1) is at least 40 nm, such as in the range of 40-150 nm. Hence, in such gap, the relative intensity is ≤k.

Optionally, the term may also refer to a plurality of gaps. In general, this will imply that in the first mode there will be a single gap, but its position may be selected. In this way, the extend and/or type of color blindness may also be met by the lighting system. Hence, in embodiments the position of the gap and/or the width of the gap may be defined by a user (via a user interface).

Therefore, in specific embodiments, the gap width may be predefined in the system. In yet further embodiments, a maximum gap width value may be predefined in the system. In embodiments, the gap width may be influenced (via a user interface) by a user (in embodiments up to a predefined maximum gap width value). Likewise, in specific embodiments, the gap position may be predefined in the system. In yet further embodiments, a number of gap positions may be predefined in the system. In embodiments, the gap position may be influenced (via a user interface) by a user. Therefore, in specific embodiments a position of the spectral intensity gap within in the spectral range of 430-600 nm is controllable.

In a second lighting mode, the lighting device also provides white light, but with an enhanced intensity within the same gap where a low or essentially zero intensity was found in the first mode. The light in the second lighting mode is especially white light, such as having a color point especially within about 15 SDCM (standard deviation of color matching) from the BBL (black body locus). The second lighting mode, may e.g. be a default mode as only a minority of people are color blind; most people are trichromatic viewers. Hence, in a second lighting mode the lighting device is configured to provide white light with a second spectral distribution with a second spectral intensity P2, with a relatively enhanced intensity P2* of the lighting device light in the same spectral range of the spectral intensity gap of the first lighting mode, wherein P2*/P2>k, such as e.g. at least >1.1*k, like at least 1.2*k.

For red-green color blind people, it appears that a position of the gap in the spectral range of 510-580 nm is beneficial. In such range, there may thus be a gap of at least 20 nm, like e.g. a gap in the range of 530-550 nm. The gap may also be broader, such as at least 50 nm, like e.g. a gap in the range of 520-570 nm. Therefore, in specific embodiments the spectral intensity gap is in the spectral range of 510-580 nm, and wherein the spectral gap width is at least 50 nm, wherein k≤0.1.

However, in other embodiments, the spectral intensity gap is in the spectral range of 440-490 nm, and the spectral gap width (GW1) is at least 20 nm, wherein k is as indicated above (such as especially k≤0.2). In this way, an oversensitivity for cyan may be compensated for.

As indicated above, the lighting system may comprise a user interface or may be functionally coupled to a user interface. Therefore, in specific embodiments the lighting system further comprising a user interface for instructing the control system. Examples of user interface devices include a manually actuated button, a display, a touch screen, a keypad, a voice activated input device, an audio output, an indicator (e.g., lights), a switch, a knob, a modem, and a networking card, among others. Especially, the user interface device may be configured to allow a user instruct the device or apparatus with which the user interface is functionally coupled by with the user interface is functionally comprised. The user interface may especially include a manually actuated button, a touch screen, a keypad, a voice activated input device, a switch, a knob, etc., and/or optionally a modem, and a networking card, etc. The user interface may comprise a graphical user interface. The term "user interface" may also refer to a remote user interface, such as a remote control. A remote control may be a separate dedicate device. However, a remote control may also be a device with an App configured to (at least) control the system or device or apparatus. For instance, a fitting room may have a button to switch (temporarily) the lighting to the first mode. Or, for instance in a grocery, a customer may use an app to switch (temporarily) the lighting to the first mode. The user interface may also be a wireless user interface.

As is clear from these examples, such switching of the device may be limited to one or more devices in a specific area. Thus, the control system may be configured to change the lighting of a subset of one or more lighting devices to the first mode while maintaining one or more subset of one or more other lighting devices in the second lighting mode (or other modes).

Therefore, in specific embodiments the lighting system further comprises a communication element for receiving instructions for the control system from a wireless user interface. In this way, the lighting system may be functionally coupled to a user interface, for instance a smart phone with an App configured to control the lighting system (more especially for allowing choosing the first mode and/or one or more of the gap width, gap position, and k-value).

In further specific embodiments, the lighting system further comprises a receiver element for receiving instructions from a wireless transmitter. For instance, the wireless transmitter may be a token or RFID chip, which may be read out by a token reader or RFID chip reader, etc. The user may receive such token or RFID for instance at entrance at a shop, or may possess such token or RFID chip personally, or an equivalent thereof. Other options of methods and devices may include wireless transmission via WiFi or NFC. Further, in specific embodiments programming of e.g. an access code and/or programming/storing user settings related to the user specific needs on the spectrum may be included. For instance, a smart phone or other personal information containing medium, like in some instance a credit card or access card, may contain the information about color blindness. Then, lighting may be (temporarily) adapted.

As indicated above, the second lighting mode may in general be the default mode. However, of course in an office or home situation, the first mode may be the default mode. Therefore in specific embodiments the lighting system comprises a basic mode (BM), wherein the second lighting mode (or optionally the first mode) is the default mode and wherein the lighting device is configured to switch to the first mode (or optionally the second lighting mode) upon a signal received by the control system and switch back to the second lighting mode (or optionally the first mode) in response to one or more of a time signal, a sensor signal and a user interface instruction. For instance, a timer may be used to switch back to the default mode after e.g. 5 minutes, or after 10 minutes, etc. This may be a fixed (predetermined) period. Hence, a time signal may trigger the return to the default mode. Of course, also a sensor may trigger the return to the default mode (or inhibit return). For instance, in a fitting room, the lighting may switch to the default mode, unless a presence sensor senses the presence of a human (which apparently has not yet left the fitting room).

In embodiments, a sensor (and control system) may be configured for detect the identity of the user, e.g. based on the recognition of a wearable device, and/or for detecting the specific spectral needs, especially in the first mode.

Alternatively or additionally, a sensor (and control system) may be configured to sense one or more of environmental light conditions (in a space comprising the lighting system), type of items (e.g. clothing) that are imaged/seen, a determination of the person (identity), etc. etc., and adapt the lighting according to predefined settings and/or relations.

The fact that there are two modes does not exclude the option that there are more than two modes. Nevertheless, the lighting devices as defined herein at least are able to provide the two lighting modes. Therefore, wherein herein is referred to the second lighting mode as default mode, this may also refer to any second lighting mode, thereby not exclude that there may be a plurality of second lighting modes. Further, it is also not excluded that the lighting devices may provide colored light, which may in embodiments also be a default mode.

The user may e.g. adapt the spectral distribution in the first mode or the second lighting mode. When adapting the spectral distribution in the first mode a color-blind person may (further) be able to fine tune the lighting to the specific desires. Hence, in embodiments the lighting system further comprises one or more light sources that are configured to provide light source light with wavelengths within the spectral intensity gap. Especially, the control system is configured to control the one or more light sources in dependence of one or more of an input signal of a user interface and a sensor. Note that this may especially apply to the first mode, though optionally this may also apply to the second lighting mode.

Hence, in specific embodiments the lighting device comprises also an (adapted) first lighting mode, wherein in response to one or more of the input signal of the user interface and the sensor at least part of the spectral intensity gap is filled with light source light. In this way, k may be increased again. Such embodiments allow a fine tuning of the lighting provided in the first mode. Lighting for color blind people may thus be personalized with the present lighting system.

Therefore, in the first lighting mode, the lighting device may provide a spectral light distribution, which may be white, and which includes a spectral intensity gap, with may optionally be filled with one or more (narrow) bands of a further light source, comprised by the lighting device, or provided by another light source from the lighting system, to provide the first spectral distribution in the first lighting mode or an adapted first lighting mode, which first spectral distribution is especially white light. In this way, in the (adapted) first mode and in the second lighting mode white light may be provided.

In specific embodiments, the lighting system further comprises a controllable band filter (or switchable optical filter) for reducing lighting device light within the spectral range of the spectral intensity gap. For instance, in embodiments a switchable cholesteric filter may be applied. In such embodiments, light may be filtered out. As indicated above, in the first mode the light may not only be filtered out, but the remainder of the spectral distribution may also change.

In addition, or alternative to filtering out, the gap may be created by not providing light in the gap. This may e.g. be obtained when a plurality of different light sources is applied, wherein one or more light sources do essentially not provide light in the spectral gap, and one or more others do. Therefore, in specific embodiments the lighting system, more especially one or more lighting device(s) (each), comprise(s) a plurality of light sources, wherein two or more subsets of each one or more light sources are configured to provide light source light with different spectral distributions, and wherein the control system is configured to control the plurality of light sources for providing the lighting device light in the first lighting mode or the second lighting mode (or a modified first lighting mode, as defined elsewhere herein (and/or a modified second lighting mode, as defined elsewhere herein)). Note that in embodiments one or more light sources may be comprised by both subsets. Further, more than two subsets may be available, for instance also for providing colored light. Therefore, in specific embodiments the plurality of light sources may comprise band emitters, each configured to provide light source light having a full width half maximum selected from the range of 10-150 nm. Examples of band emitters are solid state light sources, quantum dot based solid state light sources, etc.

In specific embodiments the first spectral distribution may be provided with a conventional broad band light source for providing white light, such as halogen based light source, with a (controllable) band filter, for generating the spectral intensity gap (in the first mode). The first spectral distribution obtained in this way, may optionally further be tuned to create a modified first spectral distribution. Hence, the lighting device may further include at least a single solid state light source.

In specific embodiments the second spectral distribution may be provided with a conventional broad band light source for providing whit light, such as halogen based light source. The second spectral distribution obtained in this way, may optionally further be tuned to create a modified second spectral distribution. Hence, the lighting device may further include at least a single solid state light source. Hence, in embodiments the lighting device may also comprises an adapted second lighting mode, wherein in response to one or more of the input signal of the user interface or a sensor the second spectral distribution may further be modified.

The first spectral distribution, or a modified first spectral distribution will especially differ in spectral distribution form the second spectral distribution. The optional modified spectral distribution will differ in spectral distribution from the first spectral distribution or a modified first spectral distribution.

The lighting device may be part of or may be applied in e.g. office lighting systems, household application systems, shop lighting systems, home lighting systems, accent lighting systems, spot lighting systems, theater lighting systems, fiber-optics application systems, projection systems, self-lit display systems, pixelated display systems, segmented display systems, warning sign systems, medical lighting application systems, indicator sign systems, decorative lighting systems, portable systems, automotive applications, (outdoor) road lighting systems, urban lighting systems, green house lighting systems, horticulture lighting, etc. etc.

In yet a further specific aspect, the invention provides a retail lighting system comprising the lighting system as defined herein, the retail lighting system comprising a plurality of system lighting devices, wherein the system lighting devices comprise one or more lighting devices and optionally one or more further lighting devices, wherein each of the one or more lighting devices comprise a basic mode, wherein the second lighting mode (or another mode which is not the first mode) is the default mode and wherein the one or more lighting devices are configured to switch to the first mode upon a signal received by the control system and switch back to the second lighting mode (or another mode which is not the first mode) in response to one or more of a time signal, a sensor signal (such as a presence sensor signal of a presence sensor, such as a PIR sensor) and a user interface instruction. Such retail lighting system allows e.g. at specific areas in a shop the lighting according to the first mode, whereas other areas may be lit according to another mode, such as the first mode. As indicated above, such retail lighting system may especially be configured to receive instructions from a remote user interface, such as an App.

BRIEF DESCRIPTION OF THE DRAWINGS

Embodiments of the invention will now be described, by way of example only, with reference to the accompanying schematic drawings in which corresponding reference symbols indicate corresponding parts, and in which.

The schematic drawings are not necessarily to scale.

DETAILED DESCRIPTION OF THE EMBODIMENTS

The lighting system may in embodiments comprise a lighting device (or a group of lighting devices) in which the emission color spectrum is highly tunable, mainly in the wavelength segments where there is a (varying) overlap in the color bands that are causing the problem (e.g. green-red, which is the majority of color deficient cases, but also blue-yellow).

For instance, such light spectrum may be created by the use of narrow band lighting devices or narrow band phosphors, which provide narrow emission bands in the total spectrum and are addressable (can be turned on/off and steered in intensity).

The lighting system may e.g. be used in specific environments, such as e.g. the inside of a shop, a fitting room in a clothing shop that is suitable for the envisioned function. So, an environment may be chosen that offers a light setting (sufficiently dimmed light) such that the method will work.

Further, a user interface for the user/customer may be provided, allowing him/her to change the illuminating light spectrum such that colors become more distinguishable. Such interface being manual (e.g. a simple rotating nob, a touchpad with icons (showing e.g. color deficiency type), or a combination of these (e.g. with coarse and fine tuning) Interfacing and steering of the system might also optionally be provided by an unobtrusive App function in e.g. a personal smartphone, which might then also contain the personal and specific color settings that are optimal for the person in case.

Optionally, a method for feedback data logging might be provided, e.g. to capture the satisfaction of the user, either the person with color deficiency (to e.g. optimize his/her personal settings), or the shop owner to learn about settings related to e.g. clothing types offered, or to tune to settings of the environments (e.g. increasing the 'effect' of the system in case of more disturbing surround light settings). For instance, setting data may be programmed, e.g. in a personal device of the color deficient person, or in the lighting management system of the shop owner, as to launch the correct (corrective) light spectrum for a specific color deficient user in a specific scenery of the shop (with e.g. specific clothing).

As indicated above, color blind people may use goggles to improve color perception. However, the method of filtering the light (subtractive method) results in a quite rough and non-personalized spectrum. Hence, it is herein amongst others suggested to use an additive method, and to compose the optimal spectrum for an individual color deficient person (or group of persons with similar/comparable characteristics). The aim is to maximally approach natural light (or the light spectrum as envisioned for a certain application) including the omission of an overlap band as to correct the color deficiency perception.

Figure 1:
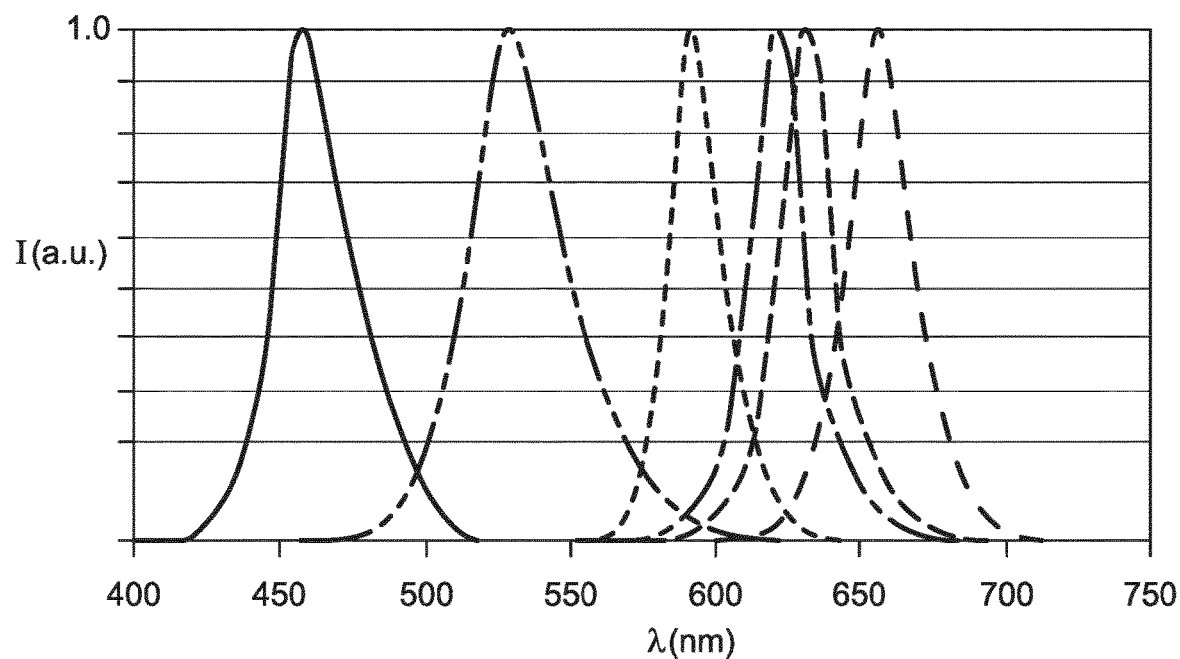
FIG. 1 schematically depict a number of possible solid state light sources.
Figure 2:
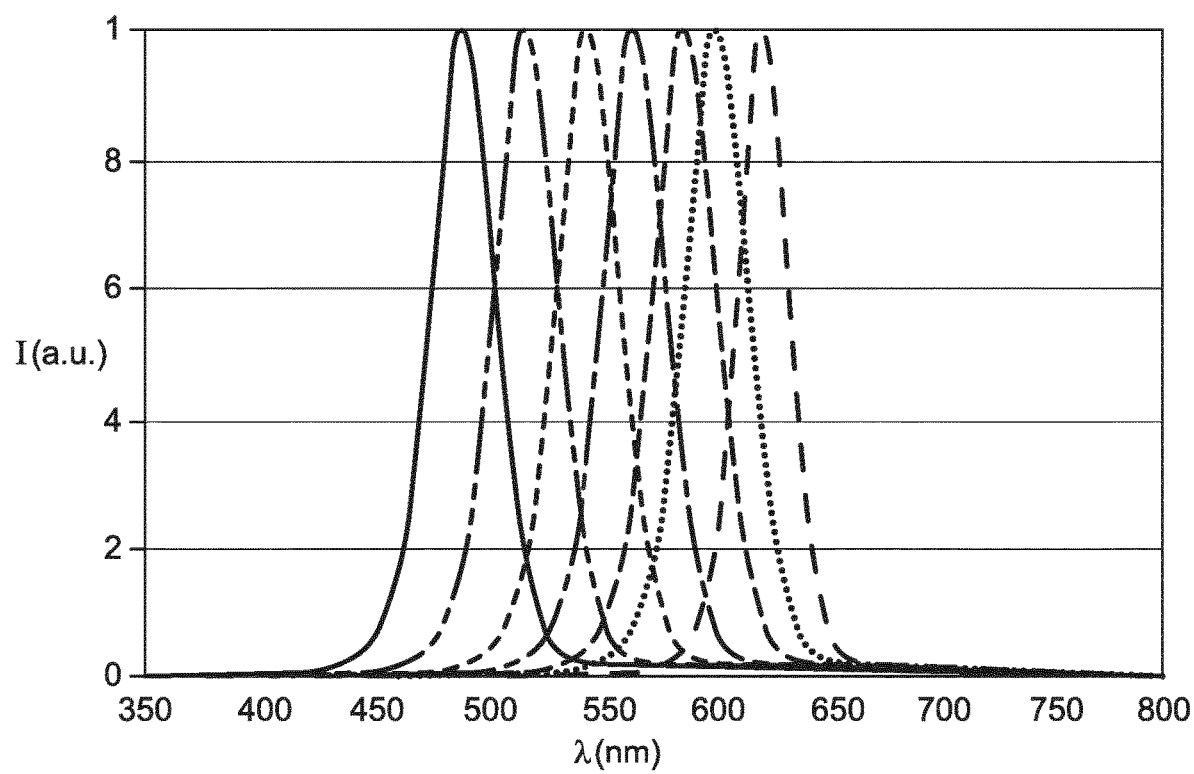
FIG. 2 schematically depict a number of QD (quantum dots) spectra, e.g. for solid state light sources using QDs for light conversion (and generation)

Several approached may be followed to create the desired spectral distributions. For instance, multiple LEDs with varying emission bands may be used, see FIG. 1. Alternatively or additionally, conversion with multiple narrow-band phosphors may be used. The spectrum would then be composed of e.g. remaining excitation light (blue) if any/wanted and the converted light. Of course, one may prevent the issue of remaining blue by using UV-emitters only for creating white spectral distributions. There are especially two options for narrow-band phosphors: either organic phosphors or the (very narrow band) Quantum Dot phosphor types. As an example, emission spectra of a set of quantum dot phosphors of one type of composition and varying geometrical size is shown in FIG. 2. Essentially, any emission maximum can be achieved by simply tuning the size of the quantum dot during fabrication.

Further, there are a number of approaches to enable the tunable spectrum functionality. For instance, in a first option a highly tunable spectrum with multiple quantum dots, based on multiple light sources in a luminaire, all these multiple light sources addressable and the light combined in a mixing luminaire. For instance, in a second option a tunable spectrum created from a baseline spectrum with 'open spectral dark regions' which dark regions are next partially filled in from a limited set of carefully selected and tuned quantum dot phosphor convertors as to approach white light as much as possible while maintaining the wanted split (black spectral region) between Green and Red. Especially option two is herein selected as most obvious approach, and a hypothetic example is used to explain the approach that could be used in the light setting.

Figure 3A:
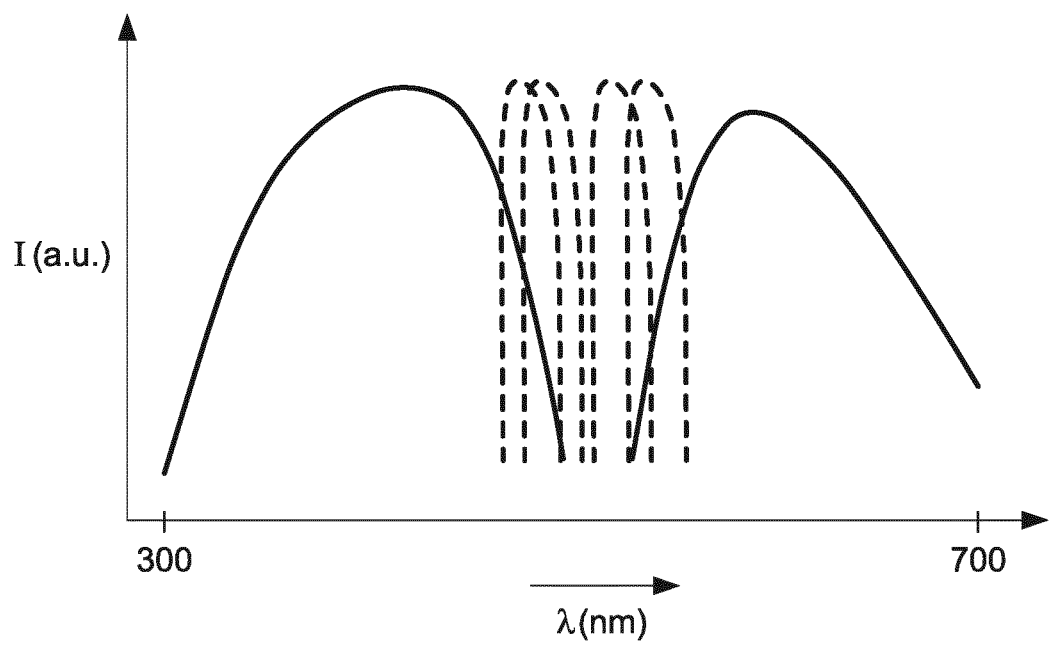
FIGS. 3a-3c schematically depict some aspects of the invention.

In FIG. 3a, an example of a base setting is shown. The base line band left and right (here called blue-green base and red base) are activated, the four (this is a hypothetical number) interlaying phosphors (or NB LED emitters) are non-active. Potentially the blue-green and red base spectra might also be tuned in intensity, also being adapted while filling in the spectrum gap, as to create an 'as good as possible' overall white spectrum (for any user or observer). This could largely prevent the color spectrum from becoming 'pinkish' and therefor noticeable and possibly disturbing. For a certain specific user, with his/her color deficiency characteristic, the optimal illumination spectrum is formed by activating (for NB phosphors: switch on the (blue or UV) excitation source, for LED emitters: switch on the power) two of the four available interlaying colors, see FIG. 3b. For another user, another spectrum might be more optimal. This is depicted in the next graph, which suggests activating another selection of spectral lines, see FIG. 3c. In this particular example in the graph the setting might be more optimal for a person that has a larger mismatch (unbalance in red and green sensitivity), so requiring a wider 'removal' of the overlapping wavelengths. As mentioned the same effect might be created by changing the (relative) intensity of the spectral band peaks.

The user may use a user interface as to allow him/her to change the light setting such that vision is improved. One might even use for that, in the fitting room, test visuals (aka Ishihara Pseudo Isochromatic Plates) to allow the user to adapt the light. But much more easily, if characteristics of person is known and color settings for the envisioned purpose would be standardized, settings might be selected with a single selection on an input device or via a smart phone that is connected to the connectivity enabled light source (and possibly already has the stored optimal setting for the user).

Figure 4:
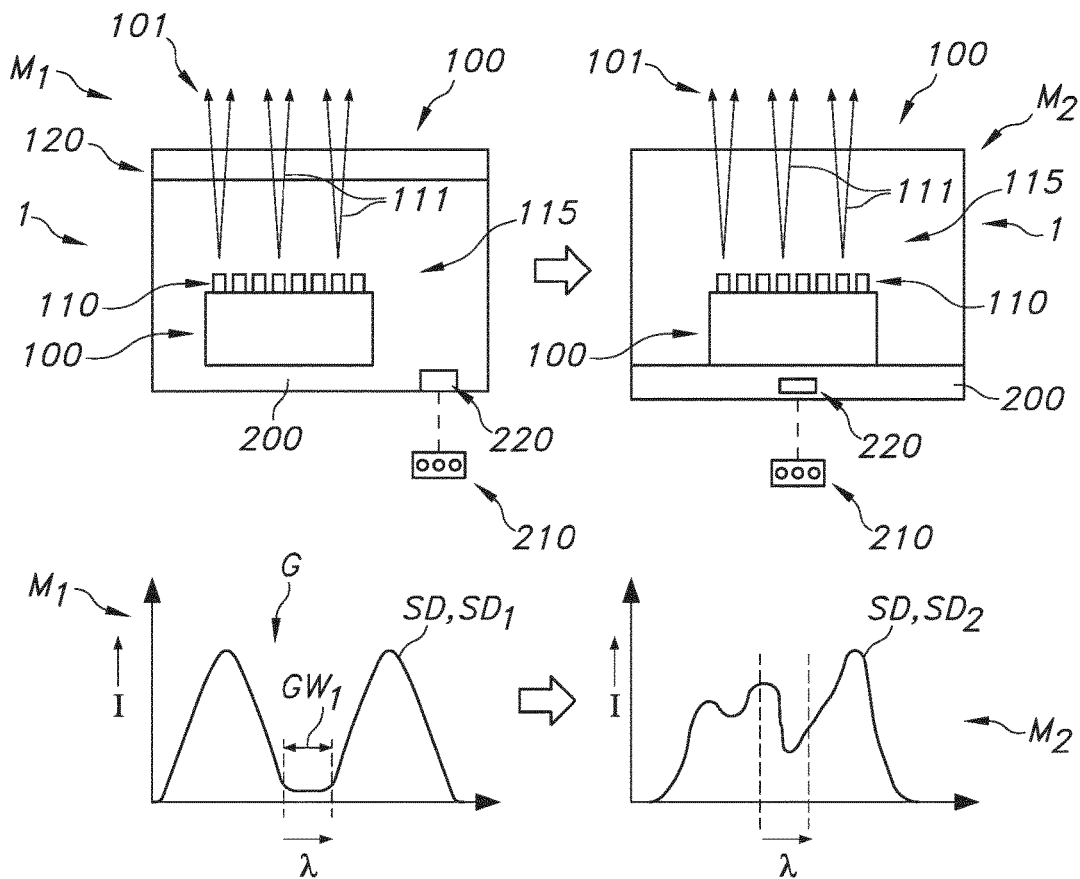
FIG. 4 schematically depict an embodiment of the lighting system and a possible first mode and a possible second lighting mode that can be achieved with such lighting system.

FIG. 4 schematically depicts an embodiment of lighting system 1, with in the upper row a change from the first mode M1 to the second lighting mode M2, and with the lower row showing a possible impact on the spectral distribution of the lighting device light 101.

The lighting system 10 comprises a lighting device 100 configured to provide lighting device light 101 with a variable spectral distribution SD, wherein the lighting system 1 comprises a control system 200 configured to control the spectral distribution SD of the lighting device light 101.

As schematically depicted, the lighting device 1 comprises at least two lighting modes M1,M2.

In a first lighting mode M1 the lighting device 1 is configured to provide (white) visible light 101 with a first spectral distribution SD1 in the visible with a first spectral intensity P1 (in number of photons), the first spectral distribution SD1 having a spectral intensity gap G configured in the spectral range of 430-600 nm, the spectral intensity gap G having a spectral gap width GW1 of at least 20 nm and a maximum spectral gap intensity PG1 (in number of photons) of lighting device light 101 within the spectral intensity gap G of PG1/P1≤k, wherein k is a predefined intensity ratio value.

In a second lighting mode M2 the lighting device 1 is configured to provide white light 101 with a second spectral distribution SD2 with a second spectral intensity P2 (in number of photons), with a relatively enhanced intensity P2* (in number of photons) of the lighting device light 101 in the same spectral range (see dashed lines) of the spectral intensity gap G of the first lighting mode, wherein P2*/P2>k.

Figure 3B:
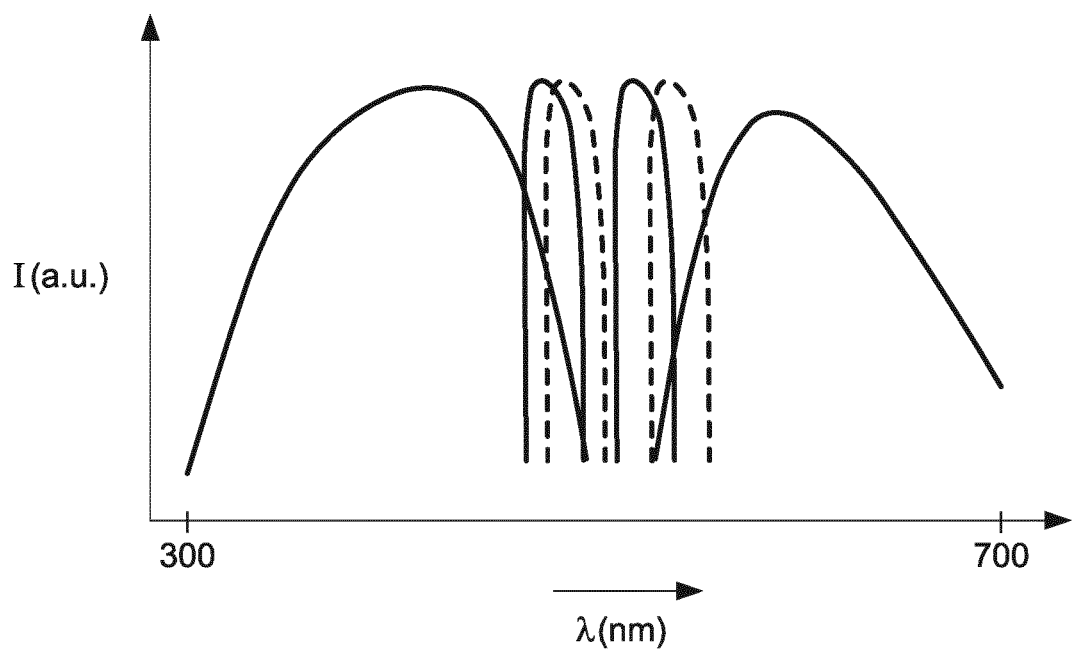
Figure 3C:
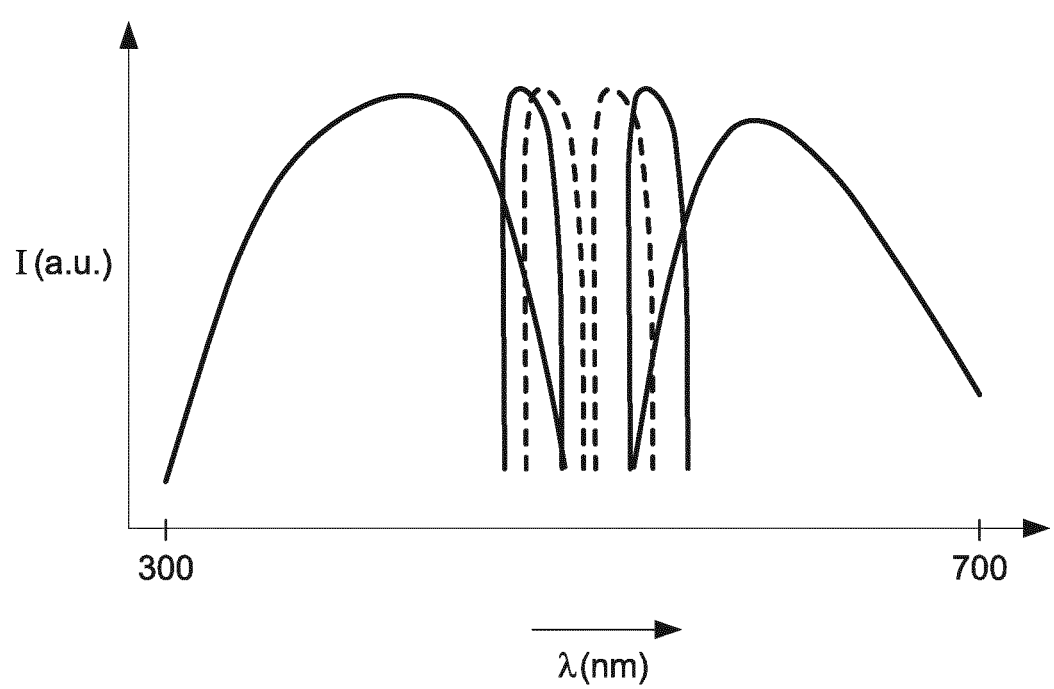
Figure 6A:
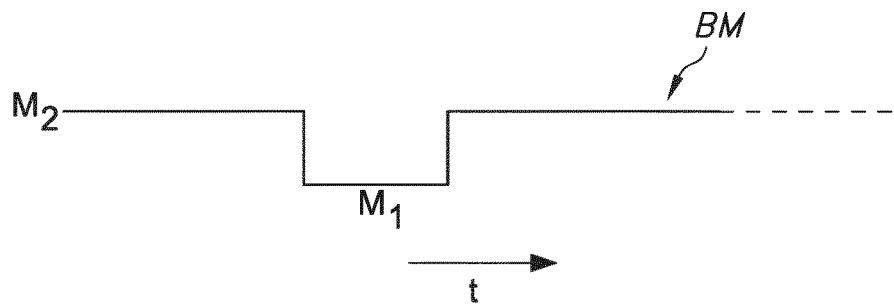
FIGS. 6a-6d schematically depict some lighting schemes.
Figure 6B:
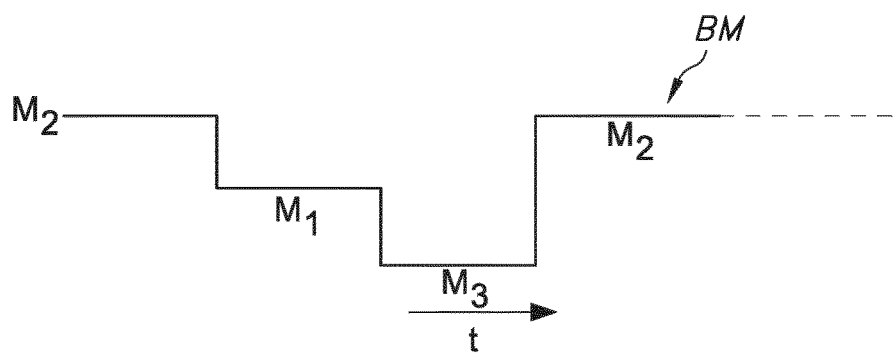
Figure 6C:
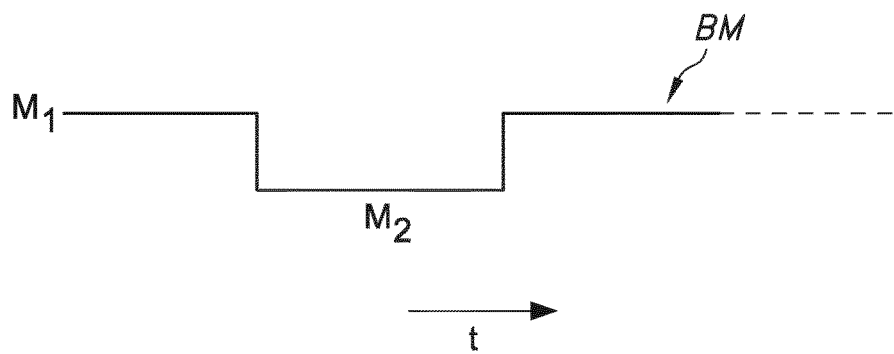
Figure 6D:
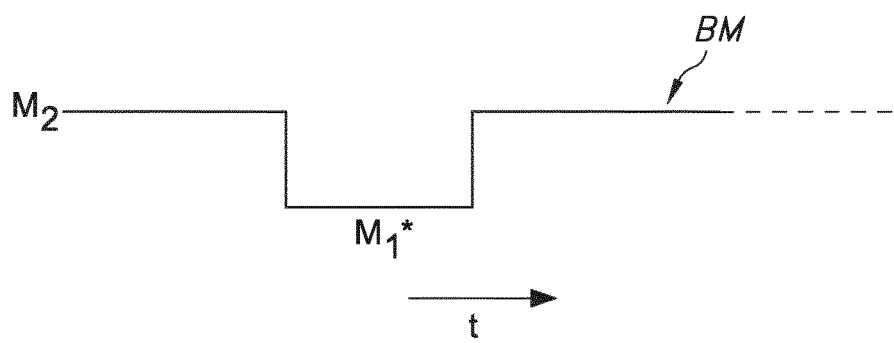

Instead of the first mode M1, which may provide or colored light, especially white light, also an adapted first mode M1* may be chosen (see also FIGS. 3b, 3c and 6d), which may especially provide white light. Hence, the lighting device may comprise an adapted first lighting mode M1* alternative or additional to the first mode M1, wherein in response to one or more of the input signal of the user interface 210 or a sensor (see also below) at least part of the spectral intensity gap G is filled with light source light (111), thereby increasing k. Examples thereof are also shown in FIGS. 3b and 3c.

Note that the lighting device light 101 may be composed of light source light 111 of a plurality of different light sources 110.

Optionally, the lighting system 1 may further comprise a controllable band filter 120 for reducing lighting device light 101 within the spectral range of the spectral intensity gap G.

Figure 5:
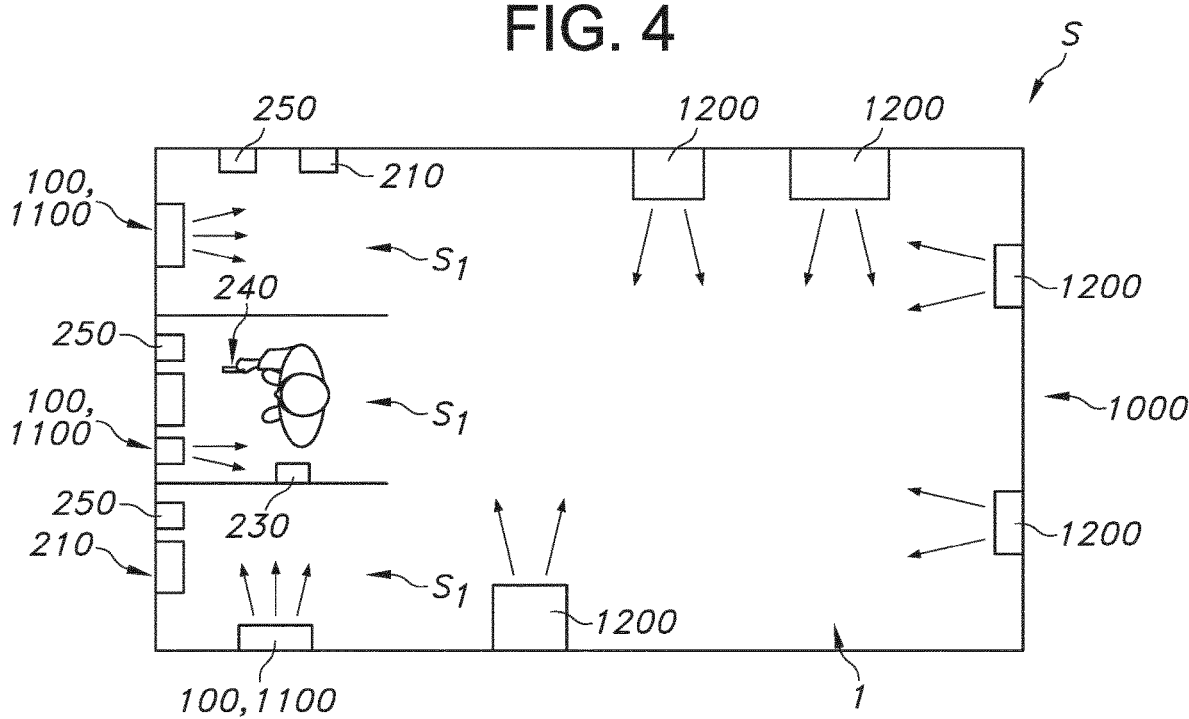
FIG. 5 schematically depict an application, such as in retail lighting.

FIG. 5 schematically depicts an application of the lighting system 1, especially as retail lighting system 1000, wherein e.g. in specific space parts S1 of a space S lighting devices 100 may be configured for customized lighting. Hence, the lighting system 1 may further comprise a user interface 210 for instructing the control system 200, such as a touch screen, or a switch, or a slide switch, etc.

Alternatively or additionally, the lighting system 1 may further comprising a communication element 220 for receiving instructions for the control system 200 from a wireless user interface 210, like an app.

In further specific embodiments, the lighting system 1 further comprises a receiver element 230 for receiving instructions (for the control system) from a wireless transmitter 240. Very schematically, the user in the middle space part S1 may carry a token, which, upon detection by the receiver element 230, instructs the control system to choose a specific spectral distribution, such as the first mode or a modified first mode.

The retail lighting system 1000 may also include other lighting devices, indicated with reference 1200. Therefore, FIG. 5 schematically depicts an embodiment of 14.

A retail lighting system 1000 comprising the lighting system 1 according to any one of the preceding claims, the retail lighting system 1000 comprising a plurality of system lighting devices 1100, wherein the system lighting devices 1100 comprise one or more lighting devices 100 and optionally one or more further lighting devices 1200, wherein each of the one or more lighting devices 100 comprise a basic mode BM, wherein the second lighting mode M2 is the default mode and wherein the one or more lighting devices 100 are configured to switch to the first mode M1 upon a signal received by the control system 200 and switch back to the second lighting mode M2 in response to one or more of a time signal, a sensor signal and a user interface instruction.

FIGS. 6a-6d schematically depict a non-limiting number of schemes, wherein switches to another mode may be triggered by a sensor signal, a user instruction, etc. Here, BM indicates a basic mode and M3 indicates another mode, e.g. non-white light.

A basic device was built and tested. It appeared that white light could be provided in both modes, one for non-color blind people, and one for color blind people, which also appears white to trichromatic people, but which gives a better color perception for the color blind test persons.

The lighting device may comprise one or more light sources. In general, the lighting device may comprise a plurality of light sources. The term "light source" may refer to a semiconductor light-emitting device, such as a light emitting diode (LEDs), a resonant cavity light emitting diode (RCLED), a vertical cavity laser diode (VCSELs), an edge emitting laser, etc. The term "light source" may also refer to an organic light-emitting diode, such as a passive-matrix (PMOLED) or an active-matrix (AMOLED). In a specific embodiment, the light source comprises a solid state light source (such as a LED or laser diode). In an embodiment, the light source comprises a LED (light emitting diode). The term LED may also refer to a plurality of LEDs. Further, the term "light source" may in embodiments also refer to a so-called chips-on-board (COB) light source. The term "COB" especially refers to LED chips in the form of a semiconductor chip that is neither encased nor connected but directly mounted onto a substrate, such as a PCB. Hence, a plurality of semiconductor light sources may be configured on the same substrate. In embodiments, a COB is a multi LED chip configured together as a single lighting module. The term "light source" may also relate to a plurality of light sources, such as 2-2000 solid state light sources.

The term "substantially" herein, such as in "substantially all light" or in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to". The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention further applies to a device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

The invention claimed is:

1. A lighting system comprising a lighting device configured to provide lighting device light with a variable spectral distribution (SD), wherein the lighting system comprises a control system configured to control the spectral distribution (SD) of the lighting device light, wherein the lighting device comprises at least two lighting modes (M1,M2), wherein:
   (i) in a first lighting mode (M1) the lighting device is configured to provide white light with a first spectral distribution (SD1) in the visible with a first spectral intensity P1, the first spectral distribution (SD1) having a spectral intensity gap (G) configured in a first spectral range of 440-490 nm or in a second spectral range of 510-580 nm, the spectral intensity gap (G) having a spectral gap width (GW1) of at least 40 nm and a maximum spectral gap intensity PG1 of lighting device light within the spectral intensity gap (G) of PG1/P1≤0.2, and
   (ii) in a second lighting mode (M2) the lighting device is configured to provide white light with a second spectral distribution (SD2) with a second spectral intensity P2, with a relatively enhanced intensity P2* of the lighting device light in the same spectral range of the spectral intensity gap (G) of the first lighting mode, wherein P2*/P2>0.2, and
   the lighting system further comprising a plurality of light sources that are configured to provide light source light with wavelengths solely within the spectral intensity gap (G), wherein the control system is configured to control the plurality of light sources in dependence of one or more of an input signal of a user interface and a sensor.

2. The lighting system according to claim 1, wherein the spectral gap width (GW1) is at least 50 nm.

3. The lighting system according to claim 1, wherein $k \leq 0.1$.

4. The lighting system according to claim 1, wherein the spectral gap width (GW1) is in the range of 40-150 nm.

5. The lighting system according to claim 1, wherein the first spectral range or the second spectral range is selected via the user interface.

6. The lighting system according to claim 1, further comprising a communication element for receiving instructions for the control system from the user interface.

7. The lighting system according to claim 1, wherein the value of the spectral gap width (GW1) and/or the ratio of the spectral gap intensity PG1 of lighting device light within the spectral intensity gap (G) of PG1/P1 is selected via the user interface.

8. The lighting system according to claim 7, wherein the lighting device comprises also an adapted first lighting mode (M1*), wherein in response to one or more of the input signal of the user interface) or the sensor at least part of the spectral intensity gap (G) is filled with light source light, thereby increasing k.

9. The lighting system according to claim 1, comprising a plurality of light sources, wherein two or more subsets of each one or more light sources are configured to provide light source light with different spectral distributions, and wherein the control system is configured to control the plurality of light sources for providing the lighting device light in the first lighting mode (M1), or the second lighting mode (M2), or a modified first lighting mode (M1*).

10. The lighting system according to claim 9, wherein the plurality of light sources comprise band emitters, each configured to provide light source light having a full width half maximum selected from the range of 10-150 nm.

11. The lighting system according to claim 1, wherein the lighting system comprises a basic mode (BM), wherein the second lighting mode (M2) is the default mode and wherein the lighting device is configured to switch to the first mode (M1) upon a signal received by the control system and switch back to the second lighting mode (M2) in response to one or more of a time signal, a sensor signal, and a user interface instruction.

12. The lighting system according to claim 1, wherein a position of the spectral intensity gap (G) within in the first spectral range of 440-490 nm or in a second spectral range of 510-580 nm is controllable.

13. The lighting system according to claim 1, further comprising a controllable band filter for reducing lighting device light within the spectral range of the spectral intensity gap (G).

14. A retail lighting system comprising the lighting system according to claim 1, the retail lighting system comprising a plurality of system lighting devices, wherein the system lighting devices comprise one or more lighting devices and optionally one or more further lighting devices, wherein each of the one or more lighting devices comprise a basic mode (BM), wherein the second lighting mode (M2) is the default mode and wherein the one or more lighting devices are configured to switch to the first mode (M1) upon a signal received by the control system and switch back to the second lighting mode (M2) in response to one or more of a time signal, a sensor signal, and a user interface instruction.

15. The retail lighting system according to claim 14, configured to receive instructions from a remote user interface.

* * * * *